(12) United States Patent
Douget et al.

(10) Patent No.: US 7,887,596 B2
(45) Date of Patent: Feb. 15, 2011

(54) DISTRACTIBLE INTERVERTEBRAL IMPLANT

(75) Inventors: Stéphane Douget, Le Bouscat (FR); Régis Le Couëdic, Andresy (FR); Gilles Larroque-Lahitette, Lagor (FR)

(73) Assignee: Zimmer Spine S.A.S., Bordeaux (FR)

( * ) Notice: Subject to any disclaimer, the term of this patent is extended or adjusted under 35 U.S.C. 154(b) by 464 days.

(21) Appl. No.: 11/820,702

(22) Filed: Jun. 20, 2007

(65) Prior Publication Data
US 2008/0009946 A1 Jan. 10, 2008

(30) Foreign Application Priority Data
Jun. 20, 2006 (FR) .................................. 06 52544

(51) Int. Cl.
*A61F 2/44* (2006.01)
*A61B 17/70* (2006.01)
(52) U.S. Cl. .............. 623/17.16; 623/17.11; 623/17.12; 623/17.13; 623/17.14; 623/17.15; 606/246
(58) Field of Classification Search .............. 623/17.11, 623/17.16; 606/62, 246
See application file for complete search history.

(56) References Cited

U.S. PATENT DOCUMENTS

| | | | |
|---|---|---|---|
| 5,480,442 A * | 1/1996 | Bertagnoli | ............... 623/17.14 |
| 6,015,436 A | 1/2000 | Schonhoffer | |
| 6,086,530 A * | 7/2000 | Mack | .......................... 600/121 |
| 6,176,881 B1 * | 1/2001 | Schar et al. | .............. 623/17.11 |
| 6,299,644 B1 | 10/2001 | Vanderschot | |

(Continued)

FOREIGN PATENT DOCUMENTS

WO    WO 98/46173 A    10/1998

OTHER PUBLICATIONS

International Search Report, PCT/FR2007/051460, Nov. 30, 2007, 4 pgs.

(Continued)

*Primary Examiner*—Thomas C Barrett
*Assistant Examiner*—Sameh Boles
(74) *Attorney, Agent, or Firm*—Sprinkle IP Law Group

(57) ABSTRACT

The invention relates to a distractible intervertebral implant having a first assembly (10) constituted by a first prosthetic plate (16) and a first spacer element (18), the prosthetic plate being secured to the first spacer element; a second assembly (12) constituted by a second prosthetic plate (22) and by a hollow second spacer element (24), having a first end secured to the second prosthetic plate and the first spacer element being suitable for sliding in the second spacer element; and means (14) for preventing the spacer element from moving in translation or in rotation relative to each other, the means having a clamping collar (28) surrounding a portion of the outside surface of the second spacer element, and a lock screw (30) for tightening the collar onto the second spacer element.

12 Claims, 2 Drawing Sheets

U.S. PATENT DOCUMENTS

| | | |
|---|---|---|
| 6,344,057 B1 | 2/2002 | Rabbe et al. |
| 6,352,556 B1 | 3/2002 | Kretschmer et al. |
| 6,375,683 B1 | 4/2002 | Crozet et al. |
| 6,454,806 B1 | 9/2002 | Cohen et al. |
| 6,524,341 B2 | 2/2003 | Lang et al. |
| 6,866,682 B1 * | 3/2005 | An et al. .................. 623/17.15 |
| 6,902,579 B2 | 6/2005 | Harms et al. |
| 6,903,485 B2 | 6/2005 | Chen et al. |
| 7,014,659 B2 | 3/2006 | Boyer, II et al. |
| 7,056,343 B2 | 6/2006 | Schafer et al. |
| 7,384,431 B2 | 6/2008 | Berry |
| 7,458,988 B2 | 12/2008 | Trieu et al. |
| 7,544,208 B1 | 6/2009 | Mueller et al. |
| 7,575,601 B2 | 8/2009 | Dickson |
| 2006/0149385 A1 | 7/2006 | McKay |
| 2007/0288092 A1 | 12/2007 | Bambakidis |

OTHER PUBLICATIONS

Written Opinion, International Searching Authority, PCT/FR2007/051460, Dec. 20, 2008, 6 pgs.
Written Opinion, International Searching Authority, PCT/FR2007/051460, English Translation, Feb. 13, 2009, 6 pgs.
International Preliminary Report on Patentability, International Searching Authority, PCT/FR2007/051460, Dec. 22, 2008, 7 pgs.
International Preliminary Report on Patentability, International Searching Authority, PCT/FR2007/051460, English Translation, Feb. 17, 2009, 7 pgs.

* cited by examiner

DISTRACTIBLE INTERVERTEBRAL IMPLANT

RELATED APPLICATION

This application claims priority to French Patent Application No. 0652544, filed Jun. 20, 2006, which application is assigned to the assignee of the present invention and the entire contents of which are incorporated herein by reference.

TECHNICAL FIELD

The present invention relates to a distractible intervertebral implant.

BACKGROUND OF THE INVENTION

So-called "replacement" intervertebral implants serve to replace one or two vertebral bodies together with their associated disks after one or two vertebrae have been removed in part. This type of implant is thus disposed between the vertebral bodies of two vertebrae. At each of its ends, the implant itself has a respective prosthetic plate for anchoring in an adjacent vertebral body, these vertebral plates usually being fitted with portions in relief firstly to provide effective anchoring of the prosthetic plates in the vertebral plates, and also to damage the plates in such a manner as to encourage bone growth within the implant itself.

Such a replacement implant is said to be "distractible" if the distance between the two prosthetic plates can be adjusted or adapted as a function of the spacing it is desired to achieve between the two vertebrae.

There exist numerous distractible intervertebral implants and they can be classified in two major categories. In the first category, there are distractible implants, which themselves include a mechanism enabling the distance between the prosthetic plates to be modified and adjusted. Those implants present the drawback of being relatively complex because of the presence of the mechanism for distracting the prosthetic plates.

In the second category, there are intervertebral implants that enable the distance between the prosthetic plates to be modified with the help of an external surgical instrument. Under such circumstances, the implant needs to have a mechanism that enables the distraction between the two plates to be maintained after the surgical distraction instrument has been removed.

In this second category, distractible intervertebral implants are known in which the prosthetic plates are mounted respectively at the ends of two cylinders that are themselves mounted telescopically. The two telescopic cylinders are prevented from moving relative to each other by known solutions using one or more cone-point screws.

It will be understood that such a system for interconnecting the cylinders on which the prosthetic plate are mounted present the drawback of not allowing the distance between the prosthetic plates to be adjusted continuously, since it is necessary to provide blind holes in the inside cylinder for receiving the cone-point screws, which are themselves mounted in the outside cylinder.

An object of the present invention is to provide a replacement intervertebral implant that is distractible in continuous manner, while presenting a structure that is mechanically simple.

SUMMARY OF THE INVENTION

To achieve this object of the invention, the implant includes a first assembly constituted by a first prosthetic plate and a first spacer element having at least a portion of its outside surface that is cylindrical, the prosthetic plate being secured to the first spacer element; a second assembly constituted by a second prosthetic plate and by a hollow second spacer element having at least a portion of its inside surface that is cylindrical, the first end of the second spacer element being secured to the second prosthetic plate and the first spacer element being suitable for sliding in the second spacer element; and means for preventing the first spacer element from moving in translation or in rotation relative to the second spacer element, the means having a clamping collar surrounding a portion of the outside surface of the second spacer element, and a lock screw for tightening the collar onto the second spacer element in such a manner that the elastic deformation of the second spacer element holds the two spacer elements together, thereby enabling the distance between the two prosthetic plates to be adjusted.

It will be understood that by means of the characteristics of the invention, once the surgeon has adjusted the distance between the two prosthetic plates using the external distraction instrument, it suffices for the surgeon to act on the screw associated with the clamping collar to ensure that the two spacer elements cannot move relative to each other. This is achieved by the elastic deformation produced by tightening the collar against the outside face of the second spacer element. It will be understood that such a fastening technique enables the distance between the prosthetic plates to be adjusted continuously.

Preferably, each prosthetic plate is removable from the spacer element that is associated therewith.

It will be understood that it is thus possible with a given pair of spacer elements to mount distinct prosthetic plates that are adapted to the particular anatomic situation.

Also preferably, each prosthetic plate presents an anchor face for anchoring in a vertebral plate, each prosthetic plate including an anchor element projecting from the anchor face.

Also preferably, each anchor element is removable from the prosthetic plate with which it is associated, and also preferably the anchor element can occupy a plurality of angular positions relative to the prosthetic plate that is associated therewith.

This disposition makes it possible to adapt the direction of the anchor element to the surgical technique used for putting the intervertebral implant into place.

In a preferred embodiment, the implant further comprises a tubular distance piece suitable for being interposed between a prosthetic plate and the first end of the spacer element that is associated therewith, in order to increase its length.

BRIEF DESCRIPTION OF THE DRAWINGS

Other characteristics and advantages of the invention appear better on reading the following description of a plurality of embodiments of the invention given as non-limiting examples. The description refers to the accompanying figures, in which.

DETAILED DESCRIPTION OF THE PREFERRED EMBODIMENTS

Figure 1:
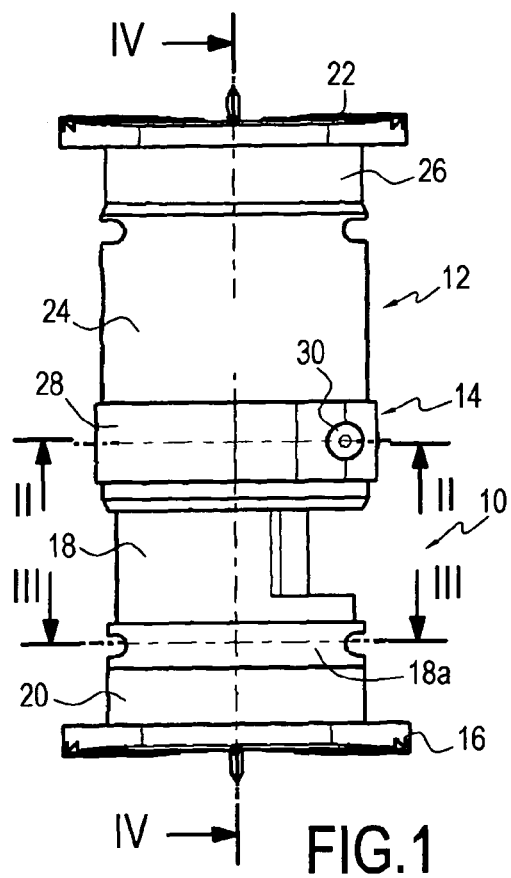
FIG. 1 is an elevation view of the vertebral implant.

As can be seen in FIG. 1, the distractible vertebral implant is constituted by a first or bottom assembly 10, by a second or top assembly 12, and by means 14 for securing the assemblies 10 and 12 to each other, and constituted in the embodiment shown by a clamping collar 14.

In the embodiment shown in FIG. 1, the first assembly 10 is constituted by a bottom prosthetic plate 16, a bottom spacer element 18, and a distance piece 20. Similarly, the second or top assembly 12 is constituted by a top prosthetic plate 22, a top spacer element 24, and a top distance piece 26. The fastener means 14 are constituted by a clamping collar 28 and a clamping screw 30.

In principle, the first spacer element or bottom spacer element 18 is mounted telescopically in the top spacer element 24. With the help of an external distracter instrument engaged in notches 25 and 27 formed at the ends of the spacer elements 18 and 24, this enables the surgeon to adjust the distance between the bottom prosthetic plate 16 and the top prosthetic plate 22 by causing the spacer element 18 to slide in the spacer element 24. When the desired spacing is reached, the surgeon can act on the clamping screw 30 to clamp the top spacer element 42 on the bottom spacer element 18 by elastically deforming the top spacer element 24. This prevents the bottom assembly 10 from moving relative to the top assembly 12. It can be understood that by preventing relative movement in this way, the distance between the two prosthetic plates can be adjusted in fully continuous manner.

The top prosthetic plate 22 has an anchor face 22a for anchoring in the vertebral plate, and in its other face it has a fastener skirt 22b. The fastener skirt 22b of the prosthetic plate 22 is engaged in an enlarged portion 26a of the distance piece 26.

The bottom prosthetic plate 16 is mounted in the bottom distance piece 20 in the same manner.

Figure 8:
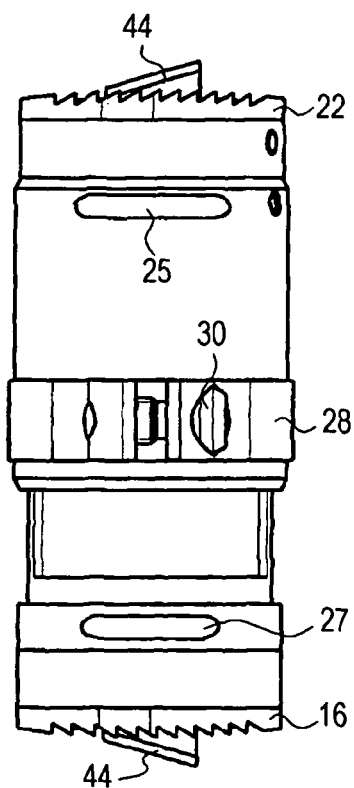
FIG. 8 is a view of the implant assembly from the side.
Figure 6:
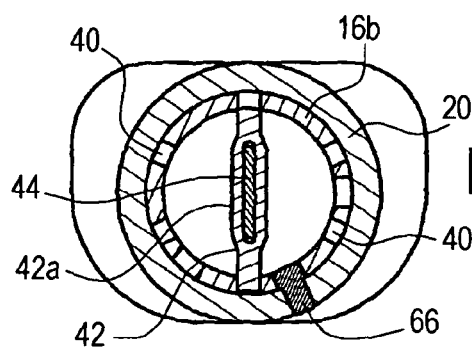
FIG. 6 is a section view on line VI-VI of FIG. 5.

The prosthetic plate 16 has pairs of notches such as 40 that are diametrically opposite, as can be seen in FIG. 6. In each pair of notches, it is possible to engage a support part 42. In the central portion 42a of the support part, there is inserted an anchor member 44 that projects from the anchor face 16a of the prosthetic plate 16. The anchor member 44 is preferably in the form of a triangular fin, as can be seen more clearly in FIG. 8. Because of the presence of the pairs of notches 40, it is possible to give the anchor fin 44 a desired angular direction. The anchor support part 42 having its ends engaged in the notches 40 of the skirt 16b is held on the axial direction of the implant by the bottom of the notch 40a and by a shoulder 46 formed in the inside face of the bottom distance piece 20.

The top prosthetic plate 22 is also fitted with a fin-shaped anchor member 44 that is mounted in the same manner as the fin of the bottom prosthetic plate 16 and that presents the same facilities for being oriented angularly.

Figure 2:
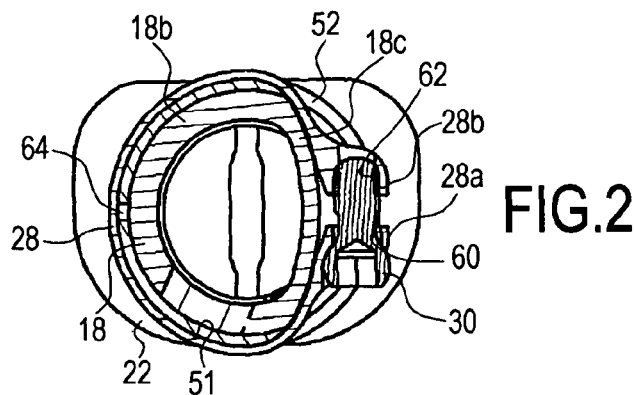
FIG. 2 is a horizontal section view on line II-II of FIG. 1.

The top distance piece 26 has a fastener skirt 26b having exactly the same shape as the fastener skirt 22b of the prosthetic plate. This skirt 26b is engaged in a portion 24a of enlarged diameter provided at the top end of the top spacer element 24. The top spacer element 24 is generally in the form of a cylinder presenting a cylindrical inside face 45. A groove 51 is formed in its outside face 50 for receiving the clamping collar 28. In order to prevent the clamping collar 28 with its screw 30 leading to a zone of greater thickness, FIG. 2 shows that the spacer element 24 level with the clamping collar presents an opening 52 in a portion of its periphery, which opening performs a function that is explained below.

Figure 4:
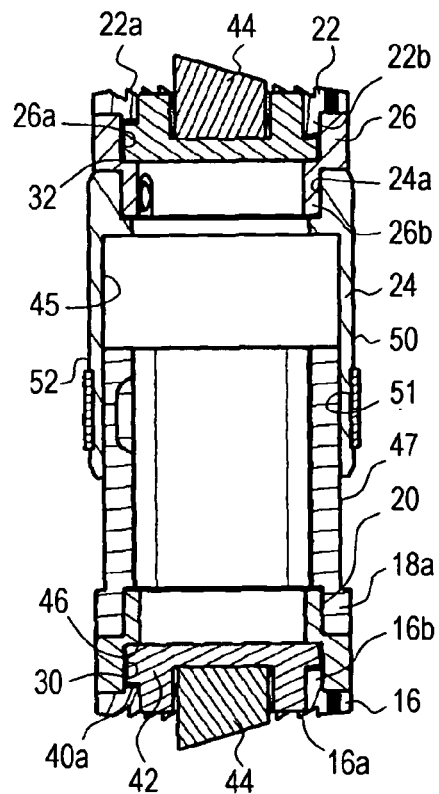
FIG. 4 is a vertical section view on line IV-IV of FIG. 1.

As shown in FIG. 4, the bottom end 18a of the spacer element 18, which is secured to the distance piece 20, is cylindrical in shape. In contrast, in its main portion, as can be seen in FIG. 2, this spacer element 18 comprises both a cylindrical portion 18b and a portion 18c having a larger radius of curvature in register with the opening 52 formed in the top spacer element 24. Thus, the clamping collar 28 surrounds the outside face of the element 24 and penetrates into it through the opening 52. The clamping collar 28 is thus pressed in part against the outside face of the top spacer element 24 and in part against the larger radius of curvature portion 18c of the spacer element 18. Since the outside face of the top spacer 24 has no relief, the direct contact between the collar and the portion of the top spacer does not disturb the continuous adjustment of the distance between the two prosthetic plates. In addition, and preferably, the top spacer element 24 has at least one opening 63 for inserting additional graft material into the internal cavity of the implant. The clamping collar 28 has two ends 28a and 28b. In the end 28a, there is formed an orifice 60 which is smooth, while in the end 28b, there is formed a tapped orifice 62. Thus, with the clamping screw 30, which is of the hollow hexagonal cylindrical type, for example, it is possible to move the ends of the clamping collar 28 towards each other, thereby elastically deforming the top spacer element 24, which is thus pressed against the outside face of the bottom spacer element 18, the clamping collar acting in part through the opening 52 against the outside face of the spacer element 18. To encourage elastic deformation spacer element 24, it may advantageously be provided with a longitudinal slot 64 that extends as far as its bottom end.

To improve the way the two spacer elements 18 and 24 are held stationary relative to each other under the action of the clamping collar, the inside face 45 of the spacer element 24 and the outside face 47 of the spacer element 18 are treated so as to increase their roughness coefficients.

Figure 3:
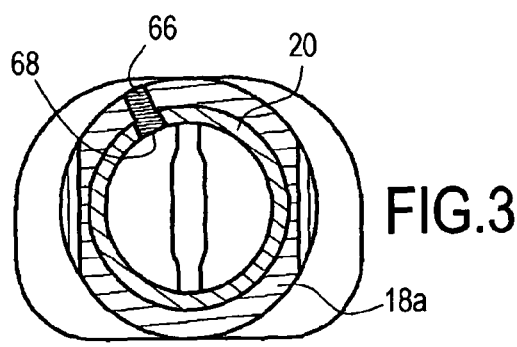
FIG. 3 is a horizontal section view on III-III of FIG. 1.
Figure 7:
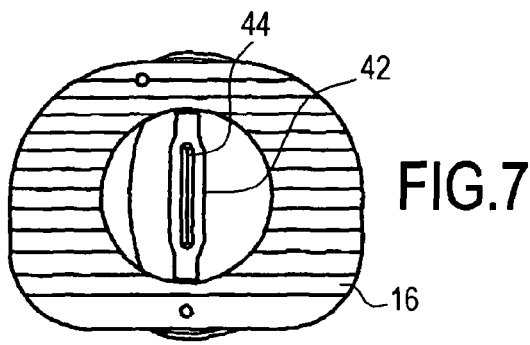
FIG. 7 is a view from beneath of the implant shown in FIG. 5.
Figure 5:
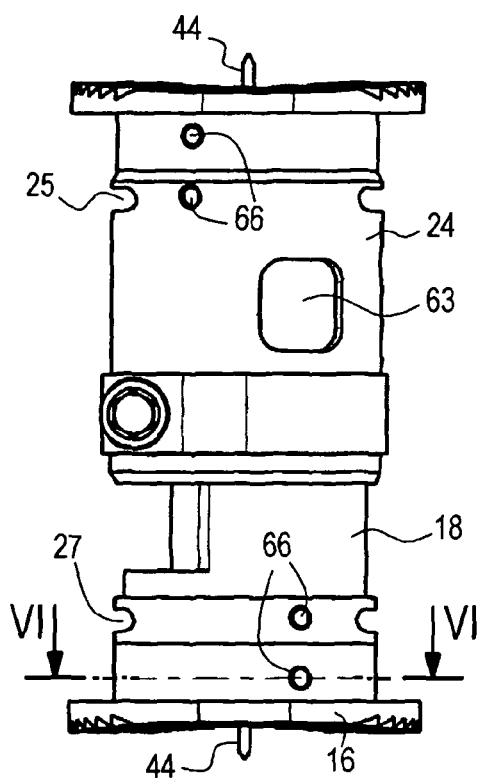
FIG. 5 is a rear elevation view of the distractible implant.

Preferably, the fastening of the prosthetic plates 16 and 22 on the distance pieces 20 and 26, and the fastening of the distance pieces 20 and 26 on the spacer elements 18 and 24 is performed by snap-fastening. As shown in FIG. 3, in order to secure the distance piece 20 with the bottom element 18a of the spacer element 18, a snap-fastening pin 66 presents one end that is secured to the bottom end 18a of the spacer element 18 and its other end penetrates into a notch 68 formed in the top edge of the distance piece 20. The same applies to the other elements for securing to one another.

In the example described, each assembly 10 or 12 is constituted by a prosthetic plate, a distance piece, and a spacer element. The distance pieces 20 and 26 are naturally used only when it is desired to achieve a considerable distance between the prosthetic plates 16 and 22. Under all other circumstances, the distance pieces are not interposed between the prosthetic plates and the spacer elements. The prosthetic plates are then mounted directly to the ends of the spacer elements 18 and 24 by snap-fastening.

In the description above, the prosthetic plates 16 and 22 are removable from the distance pieces 20 and 26, and thus from the spacer elements 18 and 24. This disposition makes it possible with a single set of spacer elements 18, 24 to put different kinds of prosthetic plates 16 and 22 into place, depending on the morphological characteristics of the patient, for example. Nevertheless, it would naturally not go beyond the ambit of the invention for the prosthetic plates to be permanently secured to the ends of the spacer elements 18 and 24.

It is also clear that the particular shapes given to the bottom spacer element 18, of section that is not circular, presents the advantage of enabling the clamping screw 30 to be inset so as to avoid it projecting out from the implant. Nevertheless, it would not go beyond the ambit of the invention if the bottom spacer element 18 were likewise cylindrical in shape.

The invention claimed is:

1. A distractible intervertebral implant comprising: a first assembly constituted by a first prosthetic plate and a first spacer element having at least a portion of its outside surface that is cylindrical, said prosthetic plate being secured to the first spacer element; a second assembly constituted by a second prosthetic plate and by a hollow second spacer element having at least a portion of its inside surface that is cylindrical and an opening in a portion of its periphery, a first end of the second spacer element being secured to the second prosthetic plate, and the first spacer element being suitable for sliding in the second spacer element; and a fastener means comprising: a clamping collar surrounding a portion of outside surface of the second spacer element and penetrating into the second spacer element through the opening, the clamping collar pressing in part against the outside surface of the second spacer element and in part through the opening against the outside surface of the first spacer element; and a lock screw for tightening said clamping collar onto the second spacer element, wherein the first spacer element continues to be suitable for sliding in the second spacer element until an elastic deformation of the second spacer element caused by the tightening of the clamping collar onto the second spacer element clamps the two spacer elements together.

2. An implant according to claim 1, wherein each prosthetic plate is removable from the spacer element that is associated therewith.

3. An implant according to claim 2, wherein a prosthetic plate is secured to the first end of a spacer element or of a distance piece by a snap-fastener device.

4. An implant according to claim 1, wherein each prosthetic plate presents an anchor face for anchoring in a vertebral plate, each prosthetic plate including an anchor element projecting from the anchor face.

5. An implant according to claim 4, wherein each anchor element is removable from the prosthetic plate with which it is associated.

6. An implant according to claim 5, wherein each anchor element and each prosthetic plate is shaped so that each anchor element can occupy a plurality of angular positions relative to the prosthetic plate that is associated therewith.

7. An implant according to claim 1 further comprising a tubular distance piece suitable for being interposed between a prosthetic plate and the first end of the spacer element that is associated therewith, in order to increase its length.

8. An implant according to claim 1, wherein the outside surface of the first spacer element and the inside surface of the second spacer element presents roughness, at least over a fraction of their length.

9. An implant according to claim 1, wherein the second spacer element presents a longitudinal slot opening out into its second end in order to facilitate elastic deformation of the second spacer element under the clamping effect of said collar.

10. An implant according to claim 1, wherein at least one of said spacer elements presents at least one opening in its side wall for receiving additional graft material in the implant.

11. An implant according to claim 1, wherein said second spacer element presents an annular groove in its outside surface for receiving said clamping collar.

12. An implant according to claim 1, wherein the outside surface of the second spacer element has no relief.

* * * * *